(12) United States Patent
Yunoki

(10) Patent No.: US 6,960,684 B2
(45) Date of Patent: Nov. 1, 2005

(54) PRODUCTION PROCESS FOR UNSATURATED ALDEHYDE

(75) Inventor: Hiromi Yunoki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 2 days.

(21) Appl. No.: 10/385,676

(22) Filed: Mar. 9, 2003

(65) Prior Publication Data

US 2003/0191344 A1 Oct. 9, 2003

(30) Foreign Application Priority Data

Mar. 29, 2002 (JP) ........................... 2002-096886

(51) Int. Cl.⁷ ............................... C07C 51/16
(52) U.S. Cl. ............... 562/547; 562/537; 562/538; 562/542; 562/546; 562/549; 568/475
(58) Field of Search .................... 562/512, 598, 562/599; 568/448, 449, 451

(56) References Cited

U.S. PATENT DOCUMENTS

| | | | |
|---|---|---|---|
| 3,801,634 A | | 4/1974 | Krabetz et al. |
| 4,837,360 A | * | 6/1989 | Kadowaki et al. .......... 562/546 |
| 5,198,581 A | | 3/1993 | Kawajiri et al. |
| 5,276,178 A | | 1/1994 | Onodera et al. |
| 6,028,220 A | | 2/2000 | Wada et al. |

FOREIGN PATENT DOCUMENTS

| | | |
|---|---|---|
| CA | 2115973 A1 | 9/1994 |
| EP | 0 614 868 A1 | 9/1994 |
| EP | 1074538 * | 2/2001 |
| JP | 53-30688 B | 8/1978 |
| JP | 63-38331 B2 | 7/1988 |
| JP | 3-294238 A | 12/1991 |
| JP | 3-294239 A | 12/1991 |
| JP | 4-217932 A | 8/1992 |
| JP | 8-3093 A | 1/1996 |
| JP | 10-168003 A | 6/1998 |

* cited by examiner

*Primary Examiner*—Johann Richter
*Assistant Examiner*—Karl Puttlitz

(57) ABSTRACT

The present invention provides a process in which, when an unsaturated aldehyde and/or an unsaturated carboxylic acid are produced by carrying out a catalytic gas phase oxidation reaction by using a fixed-bed multitubular reactor which is packed with a molybdenum-containing catalyst, the deterioration of the catalyst as located at a hot spot portion can be suppressed; so that the reaction can be continued for a long time while a high yield is maintained, regardless of where the hot spot portion occurs and also even if the concentration of a raw gas is high. An oxide and/or a complex oxide including molybdenum, bismuth, and iron as essential components are used as the catalysts, and the inside of each reaction tube of the fixed-bed multitubular reactor is divided in a tubular axial direction to thus arrange at least two reaction zones, and then these reaction zones are packed with the catalysts in such a manner that the ratio R of the apparent density of the catalyst to the true density of the catalyst (apparent density of catalyst/true density of catalyst) in each reaction zone differs from that in another reaction zone.

9 Claims, No Drawings

PRODUCTION PROCESS FOR UNSATURATED ALDEHYDE

BACKGROUND OF THE INVENTION

A. Technical Field

The present invention relates to a production process for an unsaturated aldehyde and/or an unsaturated carboxylic acid. More particularly, the present invention relates to a process comprising the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing an unsaturated aldehyde and/or an unsaturated carboxylic acid.

B. Background Art

As to a process which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with a catalyst, thereby producing an unsaturated aldehyde and/or an unsaturated carboxylic acid that correspond to each raw material, several proposals have hitherto been reported (e.g. JP-B-030688/1978, JP-B-038331/1988, JP-A-294238/1991, JP-A-294239/1991, JP-A-217932/1992, JP-A-003093/1996, and JP-A-168003/1998). Of the above, some processes are industrially carried out.

This catalytic gas phase oxidation reaction is accompanied with an extremely exothermic reaction, and therefore a local portion having an extraordinarily high temperature (which may hereinafter be referred to as a hot spot portion) occurs in a catalyst layer. Particularly, as long as the oxidation reaction is carried out by using the fixed-bed multitubular reactor, it is impossible to avoid the occurrence of the hot spot portion in the catalyst layer.

When the hot spot portion has a high temperature, it may excessively cause the oxidation reaction, resulting in a low yield, or, in the worst case, it may cause a runaway reaction. In addition, a catalyst as located at the hot spot portion is exposed to the high temperature, and therefore there is accelerated the deterioration of the catalyst, such as changes of physical properties and chemical properties of the catalyst to result in lowering its activity and the selectivity of the objective product. Particularly, in the case of a molybdenum-containing catalyst, the composition and properties of the catalyst tend to change due to sublimation of the molybdenum component, and therefore the deterioration extent of the catalyst is large.

The above problems are more striking in the case of carrying out the reaction at a high space velocity or in a high concentration of the raw gas for the purpose of enhancing the productivity of the objective product.

As to the above problems, if attention is directed to the entirety of the catalyst layer as packed in the reaction tube, then the catalyst as located at the hot spot portion is more rapidly deteriorated than a catalyst as located at the other portions, and the yield of the objective product is greatly lowered due to longtime use, so its production can be difficult to stably carry out. And then, as is aforementioned, the deterioration extent of the catalyst is particularly large in the case of the molybdenum-containing catalyst or in the case of carrying out the reaction at a high space velocity or in a high concentration of the raw gas.

Any of the aforementioned known-in-public proposals having hitherto been made is a proposal that aims at suppressing the temperature of the hot spot portion to low. However, in the case of carrying out the oxidation reaction by using the fixed-bed multitubular reactor, these proposals cannot completely prevent the occurrence of the hot spot portion in the catalyst layer and therefore have not succeeded in solving the problem such that the deterioration extent of the catalyst as located at the hot spot portion is relatively larger than that of a catalyst as located at the other portions. This problem is remarkable particularly in the case of using the molybdenum-containing catalyst or in the case of carrying out the reaction in a high concentration of the raw gas.

SUMMARY OF THE INVENTION

A. Object of the Invention

Accordingly, an object of the present invention is to provide a process in which, when the unsaturated aldehyde and/or the unsaturated carboxylic acid are produced by carrying out the catalytic gas phase oxidation reaction by using the fixed-bed multitubular reactor which is packed with the molybdenum-containing catalyst, the deterioration of the catalyst as located at the hot spot portion can be suppressed; so that the reaction can be continued for a long time while a high yield is maintained, regardless of where the hot spot portion occurs and also even if the concentration of the raw gas is high.

B. Disclosure of the Invention

The present inventor has diligently studied in order to solve the above-mentioned problems. As a result, he has taken note of a ratio R of the apparent density of the catalyst to the true density of the catalyst (apparent density of catalyst/true density of catalyst) to find out that: even if a catalyst of which this R is higher is exposed to a high temperature, the deterioration extent of this catalyst is smaller than that of a catalyst of which the R is lower. And then he has come to realize that the above problems can be solved by preparing catalysts different as to the ratio R and then packing them in such a manner that a catalyst of which the R is higher is located at the hot spot portion or in its neighborhood.

That is to say, a production process for an unsaturated aldehyde and/or an unsaturated carboxylic acid, according to the present invention, comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing the unsaturated aldehyde and/or the unsaturated carboxylic acid which correspond to the raw material; with the production process being characterized in that an oxide and/or a complex oxide including molybdenum, bismuth, and iron as essential components are used as the catalysts, and further characterized by further comprising the steps of: dividing the inside of each reaction tube of the fixed-bed multitubular reactor in a tubular axial direction to thus arrange at least two reaction zones; and then packing these reaction zones with the catalysts in such a manner that the ratio R of the apparent density of the catalyst to the true density of the catalyst (apparent density of catalyst/true density of catalyst) in each reaction zone differs from that in another reaction zone.

These and other objects and the advantages of the present invention will be more fully apparent from the following detailed disclosure.

DETAILED DESCRIPTION OF THE INVENTION

As to the catalysts, used in the present invention, which include molybdenum, bismuth, and iron as essential components, any catalyst can be used if the use thereof makes it possible to produce the corresponding unsaturated aldehyde and/or unsaturated carboxylic acid by the catalytic gas phase oxidation reaction of at least one compound selected from the group consisting of propylene, isobutylene, t-butyl alcohol, and methyl t-butyl ether as a raw material. However, favorably used is a complex-oxide catalyst of a general formula (1) below:

$$Mo_a W_b Bi_c Fe_d A_e B_f C_g D_h E_i O_x \qquad (1)$$

(where: Mo is molybdenum; W is tungsten; Bi is bismuth; Fe is iron; A is at least one element selected from among cobalt and nickel; B is at least one element selected from among sodium, potassium, rubidium, cesium, and thallium; C is at least one element selected from among boron, phosphorus, chrome, manganese, zinc, arsenic, niobium, tin, antimony, tellurium, cerium, and lead; D is at least one element selected from among silicon, aluminum, titanium, and zirconium; E is at least one element selected from among alkaline earth metals; and O is oxygen; and further, a, b, c, d, e, f, g, h, i, and x denote atomic ratios of Mo, W, Bi, Fe, A, B, C, D, E, and O respectively; and in the case of a=12, the following inequalities are satisfied: $0 \leq b \leq 5$; $0.1 \leq c \leq 10$; $0.1 \leq d \leq 20$; $1 \leq e \leq 20$; $0.001 \leq f \leq 5$; $0 \leq g \leq 10$; $0 \leq h \leq 30$; and $0 \leq i \leq 5$; and x is a numerical value as determined by the oxidation state of each element).

There is no especial limitation on starting raw materials for the above catalytic component elements. Ammonium salts, nitrates, carbonates, chlorides, sulfates, hydroxides, organic acid salts, and oxides of metal elements as generally used for this kind of catalyst or a mixture thereof in combination may be used, but the ammonium salts and nitrates are favorably used.

An aqueous solution or slurry of a blend of starting materials for the catalyst may be prepared by a process as generally used for this kind of catalyst. For example, aqueous solutions may be prepared from the above starting materials for the catalyst and then blended together in order. There is no especial limitation on conditions for blending the starting materials for the catalyst (e.g. blending order, temperature, pressure, and pH). There is also a case where the aqueous solution or slurry of the blend of the starting materials for the catalyst, as obtained in this way, is concentrated to dryness to obtain a cake solid, when the occasion demands. The aforementioned aqueous solution, aqueous slurry, or cake solid of the blend of the starting materials for the catalyst is heat-treated, thus obtaining a catalyst precursor P1.

There is no especial limitation on the heat treatment method for obtaining the catalyst precursor P1 and the form of the catalyst precursor. For example, a powdery catalyst precursor may be obtained with such as a spray dryer and a drum dryer, or a blockish or flaky catalyst precursor may be obtained by heating under a gas stream with such as a box-type dryer or a tunnel-type dryer.

The heat-treatment conditions are set in such a manner that the ignition loss ratio of the catalyst precursor P1 will be favorably in the range of 10 to 40 mass % (excluding 40 mass %), more favorably 13 to 37 mass %, still more favorably 15 to 35 mass %. However, it is naturally possible to use the catalyst precursor even if its ignition loss ratio is outside the above range.

When the catalyst precursor P1 is uniformly mixed and about 10 g thereof is accurately weighed out and then heated under air atmosphere at 300° C. for 1 hour, the ignition loss ratio of the catalyst precursor is calculated from the following equation:

ignition loss ratio (mass %)=(mass of catalyst precursor−mass of catalyst precursor after heating)/mass of catalyst precursor× 100.

The ignition loss includes: such as a nitrate radical component and an ammonium radical component that remain in the catalyst precursor P1 and become decomposed, volatilized, and sublimed by the heat treatment; and water (The nitrates and the ammonium salts as contained in the catalyst precursor P1 become decomposed by heating at high temperature and thus removed from the catalyst precursor P1. That is to say, it is meant that: the higher the ignition loss ratio of the catalyst precursor is, the higher the content of such as the nitrates and the ammonium salts in this catalyst precursor is.).

The above heat-treatment conditions should fitly be selected according to the kind or properties of a heating apparatus (dryer), and they cannot be specified sweepingly. However, for example, in the case of using the box-type dryer, the catalyst precursor may be obtained by such as carrying out heat treatment under a gas stream at a temperature of not higher than 230° C. for 3 to 24 hours.

The catalyst precursor P1, favorably, of which the ignition loss ratio has been adjusted in the above way, is subjected to a pulverization step or a classification step for obtaining a powder having appropriate particle diameters when the occasion demands, and then it is transferred to a subsequent molding step. Into the catalyst precursor P1, favorably, of which the ignition loss ratio has been adjusted in the above range, a binder is subsequently added and mixed to thus prepare a catalyst precursor P2.

There is no especial limitation on the kind of the binder as added and mixed into the catalyst precursor P1. Examples thereof include publicly known binders usable for molding of catalysts, but water is favorable.

The amount of the binder as added and mixed into the catalyst precursor P1 (favorably the amount of the water as added and mixed into the catalyst precursor P1) is favorably in the range of 5 to 30 parts by mass, more favorably 8 to 27 parts by mass, still more favorably 11 to 24 parts by mass, relative to 100 parts by mass of the aforementioned catalyst precursor P1.

In the case where the amount as added is larger than 30 parts by mass, there may be a possibility that the moldability of the catalyst precursor P2 is deteriorated to such a degree that the molding cannot be carried out. In the case where the amount as added is smaller than 5 parts by mass, there is a possibility that: the binding between the catalyst precursors P2 is so weak that the molding itself cannot be carried out or that, even if the molding can be carried out, the physical strength of the catalyst is lowered. In the case of carrying out extrusion-molding, a molding machine is broken if things come to the worst.

The water as added to the catalyst precursor P1 can be added even in the form of an aqueous solution of various substances or a mixture of various substances and water.

Examples of the substances as added together with the water include: molding assistants for enhancing the moldability; reinforcements and binders for enhancing the catalyst strength; and substances that are generally used as pore-forming agents for forming pores in the catalyst. As to these substances, favorable are substances that do not have bad influence on the catalyst performance (activity, and selectivity of the objective product) by the addition. That is to say, favorable are: (i) an aqueous solution, or a mixture with water, of a substance that does not remain in the catalyst after the calcination; and (ii) an aqueous solution, or a mixture with water, of a substance that does not have bad influence on the catalyst performance even if this substance remains in the catalyst after the calcination.

Specific examples of the above (i) include: organic compounds, such as ethylene glycol, glycerin, propionic acid, maleic acid, benzyl alcohol, propyl alcohol, butyl alcohol, and phenol; and nitric acid, ammonium nitrate, and ammonium carbonate.

Specific examples of the above (ii) include those which are generally known as reinforcements, such as silica, alumina, glass fibers, silicon carbide, and silicon nitride. In the present invention, the catalyst as produced has practically sufficient physical strength, but the above reinforcements are added thereto when the still higher physical strength is necessary.

In the case where the amount of the above substances as added is in excess, the physical strength of the catalyst is remarkably lowered, and therefore it is favorable to add them in such an amount as does not lower the physical strength of the catalyst to such an extent that the catalyst cannot be practically used as an industrial catalyst.

When the water is added in the form of the above aqueous solution of various substances or mixture of various substances and water, for example, when the molding is carried out by adding 20 parts by mass of 5 mass % aqueous ethylene glycol solution to 100 parts by mass of the catalyst precursor P1, the amount of the water as added to the P1 is calculated as follows: 20×(1−0.05)=19 parts by mass.

The catalyst as used in the present invention may be a molded catalyst as obtained by molding the catalyst precursor P2 into a definite shape, or a supported catalyst as obtained by supporting the catalyst precursor P2 on any inert support having a definite shape, or a catalyst which comprises a combination of these molded catalyst and supported catalyst, but the molded catalyst as obtained by molding the catalyst precursor P2 into a definite shape is favorable.

There is no especial limitation on the shape of the above catalyst, and the shape may be any shape of such as a spherical shape, a column shape (pellet shape), a ring shape, and an irregular shape. Needless to say, in the case of the spherical shape, it does not need to be a true sphere, but may be a substantially spherical shape. The column shape and the ring shape are also similar to this. In addition, the shape of the catalyst as packed in each reaction zone may be either identical with or different from that in another reaction zone (e.g. gas-inlet side: spherical catalyst, and gas-outlet side: pellet catalyst). However, it is usually favorable to pack the molded catalysts or supported catalysts having the same shape.

As to the size of the above catalyst, in the case where the shape of the catalyst is a spherical shape, there are favorably used those which have an average catalyst particle diameter of 1 to 15 mm, more favorably 1 to 10 mm, still more favorably 3 to 10 mm, yet still more favorably 3 to 8 mm.

The pore volume of the catalyst is favorably in the range 0.2 to 0.6 cm$^3$/g, more favorably 0.25 to 0.55 cm$^3$/g.

In the case of the supported catalyst, there is no especial limitation on the material itself of the support, and there can be used any support that is usually usable when there is produced a catalyst for producing acrylic acid by carrying out gas phase oxidation of acrolein. Specific examples of the usable support include alumina, silica, silica-alumina, titania, magnesia, silica-magnesia, silica-magnesia-alumina, silicon carbide, silicon nitride, and zeolite.

In the case of the supported catalyst, the supporting ratio of the catalyst with which each reaction zone is packed is fitly determined so as to obtain the optimum activity and selectivity in consideration of such as the conditions of the oxidation reaction, and the activity and the strength of the catalyst, but the supporting ratio is favorably in the range of 5 to 95%, more favorably 20 to 90%, particularly favorably 30 to 85%.

Incidentally, in the present invention, the supporting ratio of the catalyst can be calculated from the following equation:

supporting ratio (%)=[(mass of catalyst after calcination−mass of support)/mass of catalyst after calcination]×100.

There is no especial limitation on the heat-treatment conditions (so-called calcination conditions) during the preparation of the catalyst, either. Applicable are calcination conditions that are generally adopted in the production of this kind of catalyst. The heat-treatment temperature of the catalyst as packed in each reaction zone may be either identical with or different from that in another reaction zone. The heat-treatment temperature is favorably in the range of 350 to 600° C., more favorably 400 to 550° C., and the heat-treatment time is favorably in the range of 1 to 10 hours.

The method for molding the catalyst may be a hitherto publicly known method. Applicable are molding methods such as an extrusion-molding method, a tabletting method, a granulation method (tumbling granulation apparatuses, and centrifugal-fluid-coating apparatuses), and Marumerizer method. Of the above, the extrusion-molding method is favorable.

The production process for an unsaturated aldehyde and/ or an unsaturated carboxylic acid, according to the present invention, is characterized by comprising the steps of: dividing the inside of each reaction tube of the fixed-bed multitubular reactor in a tubular axial direction to thus arrange at least two reaction zones; and then packing these reaction zones with the catalysts in such a manner that the ratio R of the apparent density of the catalyst to the true density of the catalyst (apparent density of catalyst/true density of catalyst) in each reaction zone differs from that in another reaction zone.

Incidentally, in the present invention, the apparent density of the catalyst is calculated as follows: apparent density of catalyst=1/(1/true density+pore volume).

In addition, in the case of the so-called supported catalyst as obtained by supporting a catalytic substance on a support, only the catalytic substance is peeled off from the surface of the support by any method, and the true density and the pore volume of the catalytic substance only are measured, thus calculating the R from the above equation.

If the catalysts different as to the ratio R of the apparent density of the catalyst to its true density are packed in the above way, then, when the unsaturated aldehyde and/or the unsaturated carboxylic acid are produced by carrying out the catalytic gas phase oxidation reaction by using the fixed-bed multitubular reactor which is packed with the molybdenum-containing catalyst, the reaction can be continued for a long time while a high yield is maintained, regardless of where the hot spot portion occurs and also even if the concentration of the raw gas is high.

There is no especial limitation on the process for producing the catalysts different as to the ratio R of the apparent density of the catalyst to its true density. However, they can be produced, for example, by the following processes (1) to (4) or a combination thereof.

(1) The R can be changed by changing the ignition loss ratio of the catalyst precursor. If the ignition loss ratio is low, the formation of pores in the catalyst is little, and therefore the apparent density of the catalyst is high. And then, unless the composition of the catalyst extremely changes, the true density of the catalyst does not change even if the production process is changed. Therefore, if the ignition loss ratio is low, the R is large. To the contrary, if the ignition loss ratio is high, the apparent density of the catalyst is low, and therefore the R is small.

(2) The kind and/or amount of the pore-forming agent as added to the catalyst are controlled. If the pore-forming agent having an action of forming pores in the catalyst is added and if the amount of this addition is relatively reduced, then the apparent density becomes high, and the R becomes large. To the contrary, if the amount of the addition becomes relatively large, then the R becomes small. In addition, the R can be controlled also by changing the kind of the pore-forming agent.

(3) Although the effect of changing the R is small, if the composition of the catalyst (the kinds and addition ratios of the metals used as raw materials for the catalyst) is changed, then the true density changes, and therefore the R also changes.

(4) The R can be controlled also by changing the pressure in the molding step. For example, in the case of the tabletting, if the tabletting pressure is raised, then the R becomes large and, if the tabletting pressure is lowered, then the R becomes small. In addition, in the case of the extrusion-molding, if the extrusion pressure is raised, then the R becomes large and, if the extrusion pressure is lowered, then the R becomes small.

Although not especially limited, the ratio R of the apparent density of the catalyst, usable in the present invention, to its true density (apparent density of catalyst/true density of catalyst) is favorably in the range of 0.25 to 0.55, more favorably 0.30 to 0.50.

In the case where the ratio of the apparent density of the catalyst to the true density of the catalyst is less than 0.25, there is a case where the diffusion efficiency in the pores rises together with the increase of the pore volume. In this case, the activity of the catalyst and the selectivity of the objective product are enhanced, but there is a disadvantage in that the catalyst strength is remarkably lowered.

In the case where the ratio of the apparent density of the catalyst to the true density of the catalyst is more than 0.55, contrary to the above, the catalyst strength is enhanced, but there is a disadvantage in that the activity of the catalyst and the selectivity of the objective product are remarkably lowered.

In the present invention, the inside of each reaction tube of the fixed-bed multitubular reactor is divided in a tubular axial direction to thus arrange at least two reaction zones, and then these reaction zones are packed with the at least two catalysts different as to the ratio R as prepared by the above process.

There is no especial limitation on the method for the above packing-arrangement. Examples thereof include: packing-arrangement in such a manner that the R decreases from the gas-inlet side toward the gas-outlet side; and packing-arrangement in such a manner that, from the gas-inlet side toward the gas-outlet side, the R once increases and thereafter decreases. Favorably, the catalysts different as to the R are arranged in such a manner that the R decreases from the gas-inlet side of each reaction tube toward the gas-outlet side thereof. That is to say, the catalyst having the largest R is arranged on the gas-inlet side, and the catalyst having the smallest R is arranged on the gas-outlet side. In addition, in the packing-arrangement in such a manner that the R once increases and thereafter decreases from the gas-inlet side toward the gas-outlet side, the ratio of the layer length of the packed catalyst having the larger R on the gas-inlet side is favorably not more than 60%, more favorably in the range of 5 to 50%, still more favorably 10 to 40%, relative to the total catalyst layer length.

If the at least two catalysts different as to the ratio R of the apparent density of the catalyst to its true density (apparent density of catalyst/true density of catalyst) are arranged in the above way, then, when the unsaturated aldehyde and/or the unsaturated carboxylic acid are produced by carrying out the catalytic gas phase oxidation reaction by using the fixed-bed multitubular reactor which is packed with the molybdenum-containing catalyst, the deterioration of the catalyst as located at the hot spot portion can be suppressed; so that the reaction can be continued for a long time while a high yield is maintained, regardless of where the hot spot portion occurs and also even if the concentration of the raw gas is high. In addition, only if the catalytic activity is controlled conventionally by using the catalysts different as to the activity, there have been limitations particularly in the case where the concentration of the raw gas is high. However, if the present invention process is used, the reaction can be continued for a long time while a high yield is maintained, even if the concentration of the raw gas is high, and regardless of where the hot spot portion occurs.

In the present invention production process for the unsaturated aldehyde and/or the unsaturated carboxylic acid, it is favorable that, furthermore, the activity of the catalyst as packed in each of the at least two reaction zones differs from that in another of the at least two reaction zones.

There is no especial limitation on the process for producing the above catalysts different as to the activity, and such as hitherto publicly known processes are usable. Specific examples thereof include: a process that involves changing the kind and/or amount of at least one element selected from the group consisting of sodium, potassium, rubidium, cesium, and thallium (which is referred to as component B in the catalyst as used in the present invention); a process that involves changing the supporting ratio; a process that involves changing the calcination temperature; a method that involves changing the dilution ratio; a method that involves the combination of the supported catalyst and the molded catalyst; and a process that involves changing the particle diameters of the catalysts; and a process that involves a combination of these processes.

There is no especial limitation on the packing-arrangement method for the catalysts in the case where the at least two reaction zones are packed with the catalysts in the above manner that the activity of the catalyst in each reaction zone differs from that in another reaction zone, namely, in the case where the at least two reaction zones are packed with the catalysts in such a manner that the ratio R of the apparent density of the catalyst to the true density of the catalyst (apparent density of catalyst/true density of catalyst) in each reaction zone differs from that in another reaction zone and further that the activity of the catalyst in each reaction zone also differs from that in another reaction zone. When attention is directed to the R, examples of the packing-arrangement method for the catalysts include the aforementioned ones such as: packing-arrangement in such a manner that the R decreases from the gas-inlet side toward the gas-outlet side; and packing-arrangement in such a manner that, from the gas-inlet side toward the gas-outlet side, the R once increases and thereafter decreases. However, when attention is directed to the activity, examples of the packing-arrangement method for the catalysts include: packing-arrangement in such a manner that the activity increases in order from the gas-inlet side toward the gas-outlet side; and packing-arrangement in such a manner that, from the gas-inlet side toward the gas-outlet side, the activity once decreases and thereafter increases. Favorably, the catalysts different as to the activity are arranged in such a manner that the activity increases in order from the gas-inlet side of each reaction tube toward the gas-outlet side thereof. That is to say, the catalyst having the lowest activity is arranged on the gas-inlet side, and the catalyst having the highest activity is arranged on the gas-outlet side. In addition, in the packing-arrangement in such a manner that the activity once decreases and thereafter increases from the gas-inlet side toward the gas-outlet side, the ratio of the layer length of the packed catalyst having the higher activity on the gas-inlet side is favorably not more than 60%, more favorably in the range of 5 to 50%, still more favorably 10 to 40%, relative to the total catalyst layer length.

If the at least two catalysts different as to the activity are arranged in the above way, then, when the unsaturated aldehyde and/or the unsaturated carboxylic acid are produced by carrying out the catalytic gas phase oxidation reaction by using the fixed-bed multitubular reactor which is packed with the molybdenum-containing catalyst, the deterioration of the catalyst as located at the hot spot portion can be more suppressed; so that the reaction can be continued for a long time while a high yield is maintained, regardless of where the hot spot portion occurs and also even if the concentration of the raw gas is high.

The most favorable mode for packing-arrangement of the catalysts is that the packing-arrangement is made in such a manner that: as to the R, it decreases from the gas-inlet side toward the gas-outlet side, and, as to the activity, it increases in order from the gas-inlet side toward the gas-outlet side. There is no especial limitation on the number of the reaction zones. The larger the number of the zones is, the easier the hot spot temperature of the catalyst layer is to control. However, industrially, the aimed effect can be obtained sufficiently by adjusting the number to about 2 or about 3. In addition, as to the dividing ratio of the catalyst layer, its optimum value depends upon such as the conditions of the oxidation reaction, and the composition, shape, and size of the catalyst as packed in each layer. Therefore, the ratio cannot be specified sweepingly. The ratio may fitly be selected so as to obtain the optimum activity and selectivity as a whole.

When the catalysts are packed into each reaction tube, it is also possible that the catalyst as diluted with an inert substance is packed into each reaction zone.

There is no especial limitation on the production process which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas, thereby producing the unsaturated aldehyde and/or the unsaturated carboxylic acid which correspond to the raw material, except for using the present invention catalyst as a catalyst. This production process can be carried out with generally used apparatuses, by generally used methods, and under generally used conditions.

That is to say, the catalytic gas phase reaction in the present invention may be carried out by a conventional one-pass method or recycling method, and such as fixed-bed reactors, fluidized-bed reactors, and moving-bed reactors can be used as reactors.

As to conditions of the above reaction, the reaction may be carried out, for example, by bringing a mixed gas into contact with the present invention catalyst in the temperature range of 250 to 450° C. under a pressure of 0.1 to 1 MPa at a space velocity of 300 to 5,000 $hr^{-1}$ (STP), wherein the mixed gas includes: 1 to 15 volume % of at least one compound selected from the group consisting of propylene, isobutylene, t-butyl alcohol, and methyl t-butyl ether as a raw gas; molecular oxygen having a volume ratio of 1 to 10 times relative to this raw gas; and an inert gas (e.g. water vapor, nitrogen gas, and carbon dioxide gas) as a diluent.

The present invention process can give particularly remarkably favorable results in comparison with conventional processes under high-loading reaction conditions that aim at enhancing the productivity, for example, under conditions where: the concentration of the raw gas is higher or the space velocity is higher. Particularly, the object of the present invention can be achieved even if a high-concentration raw gas such as has a raw-gas concentration of not smaller than 7 volume % (more severely not smaller than 9 volume %) is used. (Effects and Advantages of the Invention):

When the unsaturated aldehyde and/or the unsaturated carboxylic acid are produced by carrying out the catalytic gas phase oxidation reaction by using the fixed-bed multitubular reactor which is packed with the molybdenum-containing catalyst, the present invention can suppress the deterioration of the catalyst as located at the hot spot portion; so that the reaction can be continued for a long time while a high yield is maintained, regardless of where the hot spot portion occurs and also even if the concentration of the raw gas is high.

DETAILED DESCRIPTION OF THE PREFERRED EMBODIMENTS

Hereinafter, the present invention is more specifically illustrated by the following examples of some preferred embodiments. However, the present invention is not limited to these examples in any way. Incidentally, herein each of the conversion, selectivity, and yield is defined as follows.

Conversion (mol %)=(mols of reacted starting raw material)/(mols of supplied starting raw material)×100

Selectivity (mol %)=(mols of produced unsaturated aldehyde and unsaturated carboxylic acid)/(mols of reacted starting raw material)×100

Yield (mol %)=(mols of produced unsaturated aldehyde and unsaturated carboxylic acid)/(mols of supplied starting raw material)×100

In addition, the true density and the pore volume of the catalyst were measured with the following measurement apparatuses and by the following methods:

True Density:
- Measurement apparatus: AutoPycnometer 1320 produced by Micromeritics Co., Ltd.
- Measurement method: About 4 g of catalyst was weighed out and then put into a measuring cell, and then this cell was set into the above measurement apparatus.

Pore Volume:
- Measurement apparatus: AutoPoreIII produced by Micromeritics Co., Ltd. (mercury penetration method)

Measurement method: About 2 g of catalyst was weighed out and then measured in the pressure measurement range of 0 to 414 MPa and in an equivalent time of 10 seconds.

CATALYST PRODUCTION EXAMPLE 1

Preparation of Catalyst (1)

While 10 L of pure water was heat-stirred, 1,500 g of ammonium molybdate was dissolved thereinto, and 425 g of 20 mass % silica sol was further added thereto. To this mixed liquid, a liquid as obtained by dissolving 1,236 g of cobalt nitrate, 412 g of nickel nitrate, 372 g of iron nitrate, and 5.7 g of potassium nitrate into 1,000 ml of pure water was dropwise added under vigorously stirred conditions. Subsequently, a liquid as obtained by dissolving 446 g of bismuth nitrate into an aqueous solution was dropwise added thereto under vigorously stirred conditions, wherein the aqueous solution was obtained by adding 250 ml of concentrated nitric acid to 500 ml of pure water. Then, the suspension as produced was heat-stirred, and thereby the major part of the water was evaporated, thus obtaining a cake solid. The cake solid as obtained was heat-treated with a box-type dryer (temperature of heated gas: 170° C., linear velocity of heated gas: 1.2 m/sec, and heat-treatment time: 12 hours), thus obtaining a blockish catalyst precursor. This catalyst precursor was pulverized, and thereafter its ignition loss ratio was measured. As a result, it was 18.9 mass %. Next, 50 mass % aqueous ammonium nitrate solution was added to the resultant catalyst precursor powder in a ratio of 260 g of the solution to 1 kg of the catalyst precursor powder, and the resultant mixture was kneaded for 1 hour, and thereafter the mixture was extrusion-molded into a ring shape of 6.0 mm in outer diameter, 2.0 mm in inner diameter, and 6.0 mm in height. Next, the resultant molded structure was calcined under a stream of air at 480° C. for 5 hours, thus obtaining a catalyst (1). The composition of metal elements in this catalyst except for oxygen was as follows:

catalyst (1): $Mo_{12}Co_6Ni_2Bi_{1.3}Fe_{1.3}Si_2K_{0.08}$.

The catalyst (1) had a ratio R of its apparent density to its true density (apparent density of catalyst/true density of catalyst) of 0.35.

As to the catalyst (1), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLES 2 and 3

Preparation of Catalysts (2) and (3)

Catalysts (2) and (3) were obtained respectively in the same way as of Catalyst Production Example 1 except that the amount of the 50 mass % aqueous ammonium nitrate solution as added to the catalyst precursor P1 was each changed in the preparation method of the catalyst (1) in the above Catalyst Production Example 1.

As to the catalysts (2) and (3), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 4

Preparation of Catalyst (4)

Catalyst (4) was obtained in the same way as of Catalyst Production Example 1 except that the size of the catalyst was changed to 7.0 mm in outer diameter, 2.0 mm in inner diameter, and 7.0 mm in height in the preparation method of the catalyst (1) in the above Catalyst Production Example 1.

As to the catalyst (4), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 5

Preparation of Catalyst (5)

Catalyst (5) was obtained in the same way as of Catalyst Production Example 1 except that the amount of the potassium nitrate as added was changed to 7.2 g in the preparation method of the catalyst (1) in the above Catalyst Production Example 1. The composition of metal elements in this catalyst except for oxygen was as follows:

catalyst (5): $Mo_{12}Co_6Ni_2Bi_{1.3}Fe_{1.3}Si_2K_{0.1}$.

As to the catalyst (5), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 6

Preparation of Catalyst (6)

Catalyst (6) was obtained in the same way as of Catalyst Production Example 1 except that: of the conditions of heat-treating the cake solid, the temperature of the heated gas was changed to 220° C., and the amount of the 50 mass % aqueous ammonium nitrate solution as added to the catalyst precursor P1 was changed, in the preparation method of the catalyst (1) in the above Catalyst Production Example 1.

As to the catalyst (6), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 7

Preparation of Catalyst (7)

Catalyst (7) was obtained in the same way as of Catalyst Production Example 1 except that: the amount of the potassium nitrate as added was changed to 3.6 g, the amount of the 50 mass % aqueous ammonium nitrate solution as added to the catalyst precursor P1 was changed, and the size of the catalyst was changed in the preparation method of the catalyst (1) in the above Catalyst Production Example 1. The composition of metal elements in this catalyst except for oxygen was as follows:

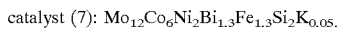

catalyst (7): $Mo_{12}Co_6Ni_2Bi_{1.3}Fe_{1.3}Si_2K_{0.05}$.

As to the catalyst (7), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 8

Preparation of Catalyst (8)

Catalyst (8) was obtained in the same way as of Catalyst Production Example 7 except that the amount of the 50 mass % aqueous ammonium nitrate solution as added to the catalyst precursor P1 was changed in the preparation method of the catalyst (7) in the above Catalyst Production Example 7.

As to the catalyst (8), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 9

Preparation of Catalyst (9)

Catalyst (9) was obtained in the same way as of Catalyst Production Example 1 except that: 9.7 g of cesium nitrate was used instead of the potassium nitrate, the amount of the 50 mass % aqueous ammonium nitrate solution as added to the catalyst precursor P1 was changed, and the size of the catalyst was changed in the preparation method of the catalyst (1) in the above Catalyst Production Example 1. The composition of metal elements in this catalyst except for oxygen was as follows:

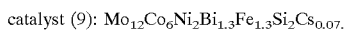

catalyst (9): $Mo_{12}Co_6Ni_2Bi_{1.3}Fe_{1.3}Si_2Cs_{0.07}$.

As to the catalyst (9), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

CATALYST PRODUCTION EXAMPLE 10

Preparation of Catalyst (10)

Catalyst (10) was obtained in the same way as of Catalyst Production Example 9 except that the amount of the 50 mass % aqueous ammonium nitrate solution as added to the catalyst precursor P1 was changed in the preparation method of the catalyst (9) in the above Catalyst Production Example 9.

As to the catalyst (10), the composition of the catalyst, the ignition loss ratio of the catalyst precursor P1, the amount of the binder as added relative to 100 parts by mass of the catalyst precursor P1, the size of the catalyst, and the ratio R of the apparent density to the true density (apparent density of catalyst/true density of catalyst) are summarized in Table 1.

Referential Examples 1 to 10

Each of the catalysts (1) to (10) as obtained in Catalyst Production Examples 1 to 10 was packed into a stainless-steel-made reaction tube of 25 mm in inner diameter (as heated with a molten nitrate) in such a manner that the layer length would be 200 mm, and then a catalytic gas phase oxidation reaction of propylene was carried out by introducing a reaction gas having the following composition at a space velocity of 1,500 $hr^{-1}$ (STP). The results are listed in Table 2.

Propylene: 3 volume %
Air: 30 volume %
Water vapor: 40 volume %
Nitrogen: 27 volume %

Example 1

The catalysts (1) and (2) were packed into a stainless-steel-made reaction tube of 25 mm in inner diameter (as heated with a molten nitrate) in order from its reaction-gas-inlet side toward its reaction-gas-outlet side in such a manner that: the layer length of the catalyst (1) would be 1,500 mm, and the layer length of the catalyst (2) would be 1,500 mm, and then a catalytic gas phase oxidation reaction of propylene was carried out by introducing a reaction gas having the following composition at a space velocity of 1,500 $hr^{-1}$ (STP). The results are listed in Table 3.

Propylene: 5.5 volume %
Air: 50.0 volume %
Water vapor: 10.0 volume %
Nitrogen: 34.5 volume %

Comparative Examples 1 to 2

The catalytic gas phase oxidation reaction was carried out in the same way as of Example 1 except that: only the catalyst (1) was packed at a layer length of 3,000 mm, or only the catalyst (2) was packed at a layer length of 3,000 mm. The results are listed in Table 3.

EXAMPLE 2, and Comparative Examples 3 and 4

Catalytic gas phase oxidation reactions were carried out in the same way as of Example 1 except that: the catalysts were packed as listed in Table 3, and the composition of the reaction gas was changed to the following composition. The results are listed in Table 3.

Propylene: 6.5 volume %
Air: 57.0 volume %
Water vapor: 10.0 volume %
Nitrogen: 26.5 volume %

EXAMPLES 3 to 5, and Comparative Example 5

Catalytic gas phase oxidation reactions were carried out in the same way as of Example 1 except that: the catalysts were packed as listed in Table 3, and the composition of the reaction gas was changed to the following composition. The results are listed in Table 3.

Propylene: 8.0 volume %
Air: 70.0 volume %
Water vapor: 10.0 volume %
Nitrogen: 12.0 volume %

TABLE 1

| Catalyst number | Composition of catalyst | Ignition loss ratio of catalyst precursor Pl (mass %) | Amount of binder as added (parts by mass) | Catalyst size Outer diameter × inner diameter × height (mm) | R (apparent density of catalyst/true density of catalyst) |
|---|---|---|---|---|---|
| (1) | $Mo_{12}Co_6Ni_2Bi_{13}Fe_{13}Si_2K_{0.08}$ | 18.9 | 26 | 6.0 × 2.0 × 6.0 | 0.35 |
| (2) | ↑ | 18.8 | 40 | ↑ | 0.30 |
| (3) | ↑ | 19.0 | 20 | ↑ | 0.43 |
| (4) | ↑ | 19.0 | 26 | 7.0 × 2.0 × 7.0 | 0.35 |
| (5) | $Mo_{12}Co_6Ni_2Bi_{13}Fe_{13}Si_2K_{0.1}$ | 19.1 | 26 | 6.0 × 2.0 × 6.0 | 0.35 |
| (6) | $Mo_{12}Co_6Ni_2Bi_{13}Fe_{13}Si_2K_{0.08}$ | 2.1 | 42 | ↑ | 0.56. |
| (7) | $Mo_{12}Co_6Ni_2Bi_{13}Fe_{13}Si_2K_{0.05}$ | 18.8 | 40 | 5.5 × 2.0 × 5.5 | 0.31 |
| (8) | ↑ | 19.0 | 26 | ↑ | 0.35 |
| (9) | $Mo_{12}Co_6Ni_2Bi_{13}Fe_{13}Si_2Cs_{0.07}$ | 19.1 | 20 | 7.0 × 2.0 × 7.0 | 0.42 |
| (10) | ↑ | 18.9 | 26 | ↑ | 0.35 |

TABLE 2

| Referential Example | Catalyst number | R (apparent density of catalyst/true density of catalyst) | Reaction temperature (° C.) | Conversion of propylene (mol %) | Total yield of acrolein and acrylic acid (mol %) | Total selectivity of acrolein and acrylic acid (mol %) |
|---|---|---|---|---|---|---|
| Referential Example 1 | (1) | 0.35 | 310 | 98.2 | 92.4 | 94.1 |
| Referential Example 2 | (2) | 0.30 | 310 | 98.3 | 92.1 | 93.7 |
| Referential Example 3 | (3) | 0.43 | 310 | 96.8 | 91.8 | 94.8 |
| Referential Example 4 | (4) | 0.35 | 310 | 97.0 | 91.7 | 94.5 |
| Referential Example 5 | (5) | 0.35 | 310 | 96.7 | 91.5 | 94.6 |
| Referential Example 6 | (6) | 0.56 | 310 | 80.5 | 76.3 | 94.8 |
| Referential Example 7 | (7) | 0.31 | 310 | 99.3 | 90.6 | 91.2 |
| Referential Example 8 | (8) | 0.35 | 310 | 99.1 | 89.8 | 90.6 |
| Referential Example 9 | (9) | 0.42 | 310 | 81.2 | 77.9 | 95.9 |
| Referential Example 10 | (10) | 0.35 | 310 | 82.3 | 78.5 | 95.4 |

TABLE 3

| | Method for packing catalysts (gas-inlet side → gas-outlet side) | Reaction time (hours) | Reaction temperature (° C.) | Conversion of propylene (mol %) | Total yield of acrolein and acrylic acid (mol %) | Total selectivity of acrolein and acrylic acid (mol %) |
|---|---|---|---|---|---|---|
| Example 1 | catalyst(1)/catalyst(2) = 1500 mm/1500 mm | 100 | 310 | 98.5 | 91.7 | 93.1 |
| | | 4000 | 315 | 98.3 | 92.6 | 94.2 |
| Comparative Example 1 | catalyst(1) = 3000 mm | 100 | 310 | 98.4 | 91.8 | 93.3 |
| | | 4000 | 314 | 98.3 | 92.0 | 93.6 |
| Comparative Example 2 | catalyst(2) = 3000 mm | 100 | 310 | 98.5 | 91.5 | 92.9 |
| | | 4000 | 322 | 98.1 | 92.1 | 93.9 |
| Example 2 | catalyst(3)/catalyst(1) = 1000 mm/2000 mm | 100 | 310 | 97.8 | 91.3 | 93.4 |
| | | 4000 | 316 | 97.9 | 91.7 | 93.7 |
| Comparative Example 3 | catalyst(4)/catalyst(1) = 1000 mm/2000 mm | 100 | 310 | 97.7 | 90.9 | 93.0 |
| | | 4000 | 321 | 97.6 | 90.9 | 93.1 |
| Comparative Example 4 | catalyst(5)/catalyst(1) = 1000 mm/2000 mm | 100 | 310 | 97.8 | 90.7 | 92.7 |
| | | 4000 | 323 | 97.6 | 90.6 | 92.8 |
| Example 3 | catalyst(6)/catalyst(1) = 1000 mm/2000 mm | 100 | 320 | 97.6 | 89.5 | 91.7 |
| | | 4000 | 334 | 97.7 | 89.8 | 91.9 |
| Example 4 | catalyst(9)/catalyst(1)/catalyst(7) = 1000 mm/1400 mm/600 mm | 100 | 320 | 99.0 | 91.0 | 91.9 |
| | | 4000 | 329 | 99.2 | 91.2 | 91.9 |
| Comparative Example 5 | catalyst(10)/catalyst(1)/catalyst(8) = 1000 mm/1400 mm/600 mm | 100 | 320 | 99.2 | 90.5 | 91.2 |
| | | 4000 | 337 | 99.0 | 89.9 | 90.8 |
| Example 5 | catalyst(1)/catalyst(9)/catalyst(2) = 200 mm/900mm/1900 mm | 100 | 320 | 99.2 | 90.6 | 91.3 |
| | | 4000 | 334 | 99.0 | 90.8 | 91.7 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for an unsaturated aldehyde and an unsaturated carboxylic acid, which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed bed multitubular reactor which is packed with catalysts, thereby producing the unsaturated aldehyde and the unsaturated carboxylic acid which correspond to the raw material;

wherein an oxide and/or complex oxide including molybdenum, bismuth, and iron as essential components are used as the catalysts, and further with the production process further comprising the steps of: dividing the inside of each reaction tube of the fixed-bed multitubular reactor in a tubular axial direction to thus arrange at least two reaction zones; and then packing these reaction zones with the catalysts in such a manner that the ratio R of the apparent density of the catalyst to the true density of the catalyst (apparent density of catalyst/true density of catalyst) in each reaction zone differs from that in another reaction zone.

2. A production process according to claim 1, wherein the at least two reaction zones are packed with the catalysts different as to the ratio R in such a manner that the R decreases from the gas-inlet side of each reaction tube toward the gas-outlet side thereof.

3. A production process according to claim 1, wherein the activity of the catalyst as packed in each of the at least two reaction zones differs from that in another of the at least two reaction zones.

4. A production process according to claim 3, wherein the at least two reaction zones are packed with the catalysts different as to activity in such a manner that the activity increases from the gas-inlet side of each reaction tube toward the gas-outlet side thereof.

5. A production process according to claim 1, wherein the reaction zones are 2 or 3 in number.

6. A production process according to claim 1, wherein the at least two reaction zones are packed with the catalysts different as to the ratio R in such a manner that, from the gas-inlet side toward the gas-outlet side, the ratio R once increases and thereafter decreases.

7. A production process according to claim 1, wherein the at least two reaction zones are packed with a catalyst different as to the ratio R in such a manner that, the reaction zone having the catalyst with the largest ratio R is arranged on the gas-inlet side and the reaction zone having the catalyst with the smallest ratio R is arranged on the gas-outlet side.

8. A production process for an unsaturated aldehyde and an unsaturated carboxylic acid, which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing the unsaturated aldehyde and the unsaturated carboxylic acid which correspond to the raw material;

wherein an oxide and/or complex oxide including molybdenum, bismuth, and iron as essential components are used as the catalysts, and further with the production process further comprising the steps of: dividing the inside of each reaction tube of the fixed-bed multitubular reactor in a tubular axial direction to thus arrange at least two reaction zones; and then packing these reaction zones with the catalysts in such a manner that the ratio R of the apparent density of the catalyst to the true density of the catalyst (apparent density of catalyst/true density of catalyst) in the most gas-outlet side reaction zone is lower than that in the second reaction zone from the gas-outlet side.

9. A production process according to claim 8, wherein the activity of the catalyst as packed in the most gas-outlet side reaction zone is higher than that in the second reaction zone from the gas-outlet side.

* * * * *